United States Patent
Bard

(10) Patent No.: US 6,553,994 B2
(45) Date of Patent: Apr. 29, 2003

(54) ORTHOPAEDIC SUPPORT

(75) Inventor: Maurice R. Bard, Markham (CA)

(73) Assignee: IWI Ltd., Markham ( * ) Notice: Subject to any disclaimer, the term of this patent is extended or adjusted under 35 U.S.C. 154(b) by 0 days.

(21) Appl. No.: 09/885,075

(22) Filed: Jun. 21, 2001

(65) Prior Publication Data

US 2003/0056792 A1 Mar. 27, 2003

(51) Int. Cl.[7] ............................................... A61G 15/00
(52) U.S. Cl. ........................................ 128/845; 602/18
(58) Field of Search ................................. 128/845, 846, 128/869, 877, 878, 879; 602/4, 5, 12, 13, 18, 20, 21, 23, 27, 60

(56) References Cited

U.S. PATENT DOCUMENTS

| 4,084,586 A | * | 4/1978 | Hettick | 128/80 C |
| 4,573,456 A | * | 3/1986 | Spann | 128/80 R |
| 5,423,087 A | * | 6/1995 | Krent | 2/2 |

\* cited by examiner

Primary Examiner—Michael A. Brown

(57) ABSTRACT

An orthopaedic support having a substrate having a series of channels in one surface thereof with a series of vent holes in the channels to promote heat dissipation through the substrate. The channels provide cooling of the skin in contact with the orthopaedic support without rendering the substrate prone to damage. Vent holes are located in the channels to provide venting through the orthopaedic support and the dissipation of heat.

12 Claims, 5 Drawing Sheets

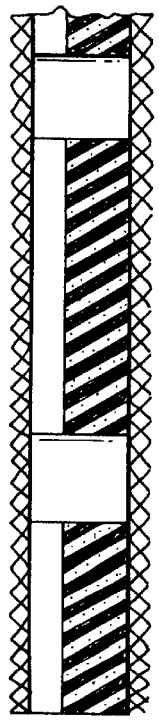
FIG.1.
FIG.3.
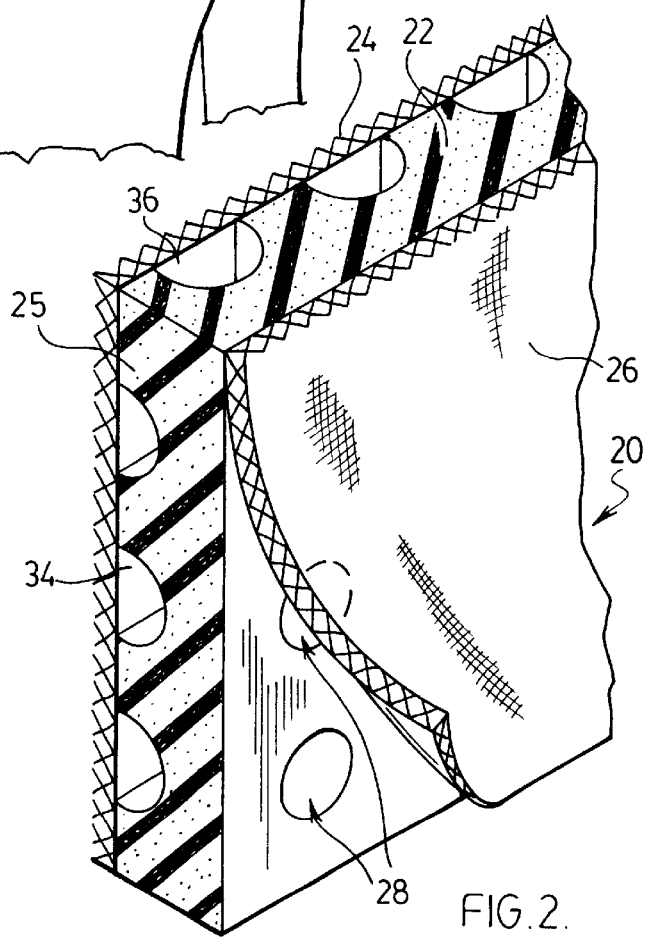
FIG.2.

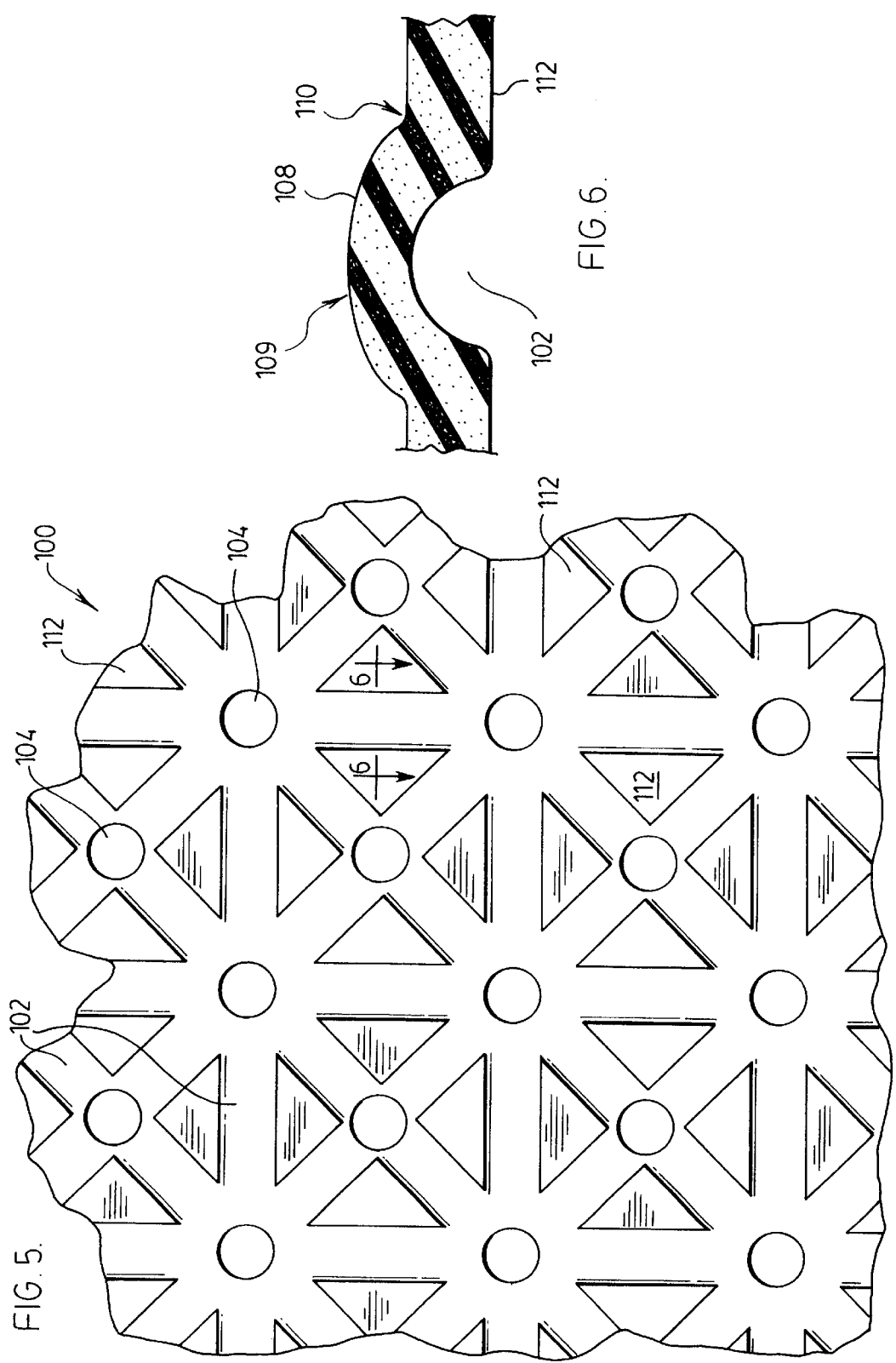

ORTHOPAEDIC SUPPORT

FIELD OF THE INVENTION

The present invention relates to orthopaedic supports and in particular, relates to a composite substrate for orthopaedic supports having improved breathability.

BACKGROUND OF THE INVENTION

Neoprene layers have been used for orthopaedic supports as they have the ability to stretch and are initially relatively comfortable. Typically, the neoprene layer has a cloth fibre layer on the surface thereof to improve the comfort. Unfortunately, neoprene or other closed cell foam layers are not breathable and tend to retain heat about the body part. Initial heat retention can be advantageous as it warms the particular body part, however, over an extended period of time, it leads to discomfort, possible skin rashes, and is not desirable. These poor operating characteristics often contribute to the orthopaedic support not being used.

It has been known to use a closed cell foam structure with a breathable fabric either side to improve the characteristics of the composite material. Unfortunately, the closed cell foam acts as an excellent thermal insulation and excess heat and moisture typically occurs.

U.S. Pat. No. 5,620,771 discloses a specialized orthopaedic substrate layer which has a series of pin holes with each pin hole acting as a pressure release valve which vents when sufficient pressure is achieved. This structure also tends to maintain moisture and maintain heat.

The present invention seeks to overcome the shortcomings described above.

SUMMARY OF THE INVENTION

An orthopaedic support according to the present invention comprises a composite substrate for fastening about a body part with the composite substrate comprising a foam cellular layer with a series of interconnecting channels in one side thereof. A series of holes extend through the foam cellular layer and provide improved venting and air circulation. The composite substrate includes a breathable layer covering the one side of the foam cellular layer and this breathable layer cooperates with the channels and the series of holes to provide air circulation through the composite substrate and through the channels.

It has been found that the composite substrate as described above provides improved air circulation through the substrate. The additional movement of the body part associated with the orthopaedic support expands or compresses the composite substrate and provide a pumping action further promoting air exchange through the substrate.

According to a further aspect of the invention, the composite substrate includes a breathable fabric on an exterior surface of the closed cell foam layer opposite the breathable layer.

According to yet a further aspect of the invention, the orthopaedic support is reversible to alter the heat retention characteristic of the orthopaedic support.

In yet a further aspect of the invention, the channels are selected from longitudinal channels, lateral channels and diagonal channels.

In yet a further aspect of the invention, the longitudinal channels, lateral channels and diagonal channels intercept with some of the series of holes through the foam cellular layer.

In yet a further aspect of the invention, the foam cellular layer is made of neoprene.

In yet a further aspect of the invention, the channels occupy less than 25 percent of the one side of the foam cellular layer.

BRIEF DESCRIPTION OF THE DRAWINGS

Preferred embodiments of the invention are shown in the drawings, wherein:

FIG. 1 is a partial perspective view showing a neck orthopaedic support applied to a user;

FIG. 2 is a partial exploded view showing the different layers of the composite substrate;

FIG. 3 is a sectional view through the composite substrate showing the interconnection of the channels and holes;

FIG. 5 is a bottom view of a modified substrate;

FIG. 6 is a partial sectional view along line 6—6 of FIG. 5;

DETAILED DESCRIPTION OF THE PREFERRED EMBODIMENTS

Figure 4:
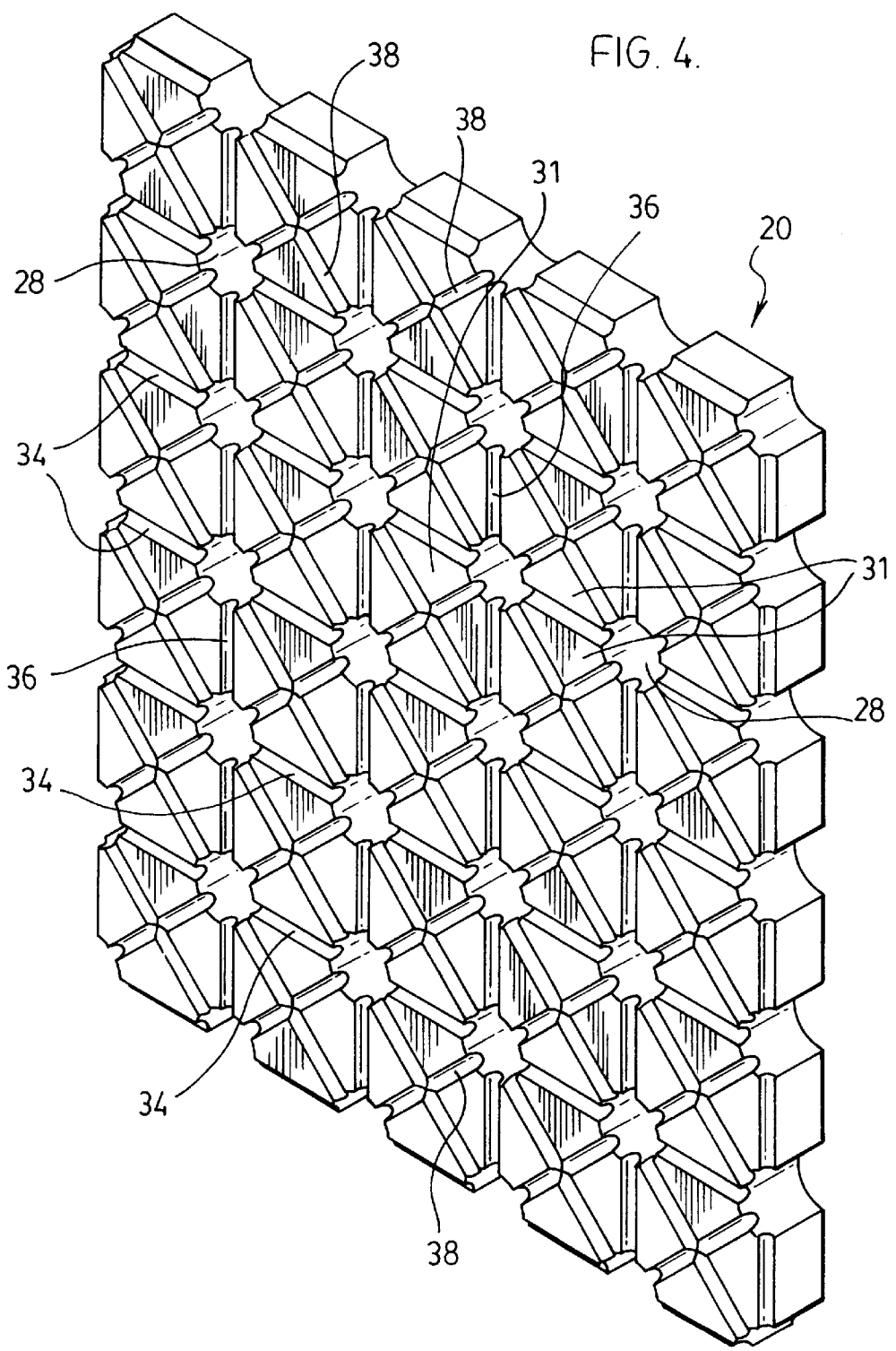
FIG. 4 is a partial perspective view of the closed cell foam layer with various channels and holes provided on one side of this layer.
Figure 7:
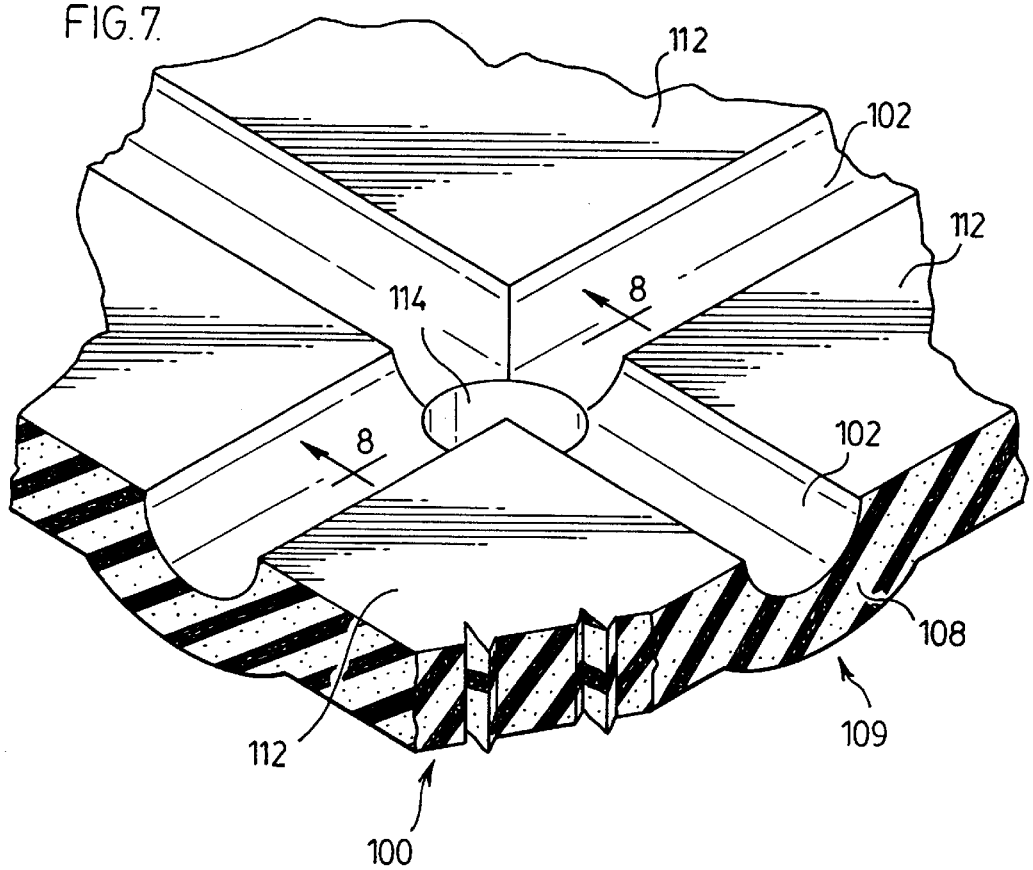
FIG. 7 is a partial perspective view of the diagonal channels and the modified substrate.
Figure 8:
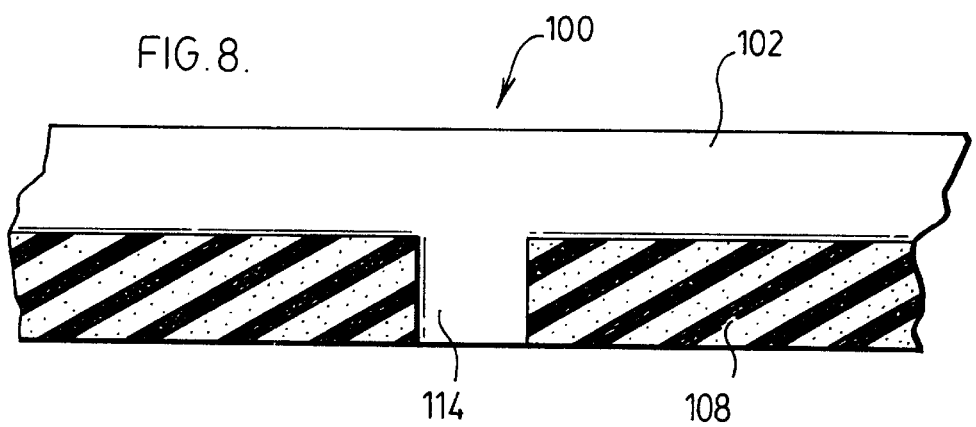
FIG. 8 is a section view along line 8—8 of FIG. 7.

The orthopaedic support 2 is shown applied about the neck 4 of the user 6. As can be appreciated, this orthopaedic support is suitable for a host of different applications including, for example, knee supports, elbow supports, ankle supports, and back supports.

The orthopaedic support is preferably made of a composite substrate 20 comprising a foam cellular layer 22, an exterior fabric breathable layer 26, and an interior breathable fabric layer 24. The foam cellular layer 22 has a series of holes 28 through the layer to allow venting to the exterior of the substrate. Often the foam cellular layer is a closed cell foam layer. The interior surface 25 of the foam substrate 22 has a series of longitudinal channels 34, a series of lateral channels 36, and a series of diagonal channels 38. These channels all open onto the holes 28 and provide venting of the interior surface of the orthopaedic support through the holes 28 to the exterior. The breathable fabric layer 24 provides a more comfortable layer to be applied against the skin of the user and also assists in allowing venting to one of the channels and eventually through the holes 28.

Although closed cell neoprene is preferred, other materials and open foams can be used, and provide the required support.

As clearly shown in FIG. 4, the interior surface of the foam layer which is preferably of neoprene, has been broken into small island portions 31 which provide a contact surface for adhering to the breathable layer 24. With these small regions, the channels surround these regions and promote air circulation and the venting of heat and moisture. Any compressive or relaxing movement of the orthopaedic support caused by the user bending that particular body part will promote increased air circulation through the orthopaedic support.

For example, if the substrate is compressed, air will be exhausted through the holes 28 and when the compressive force is removed, the substrate will return to its original condition and draw new air into the channels through the holes 28. In addition, the natural tendency of the orthopaedic support will provide some air circulation even without this pumping action.

The island portions 31 provide a support network which contacts the skin of the user. Some compression will occur but the channels remain functional and remove heat acting as a cool boundary to the islands.

With this arrangement, the desirable comfort and heat retaining capability of the neoprene is used to allow initial warm up and maintaining a comfortable heat level with respect to the particular body part while allowing ventilation and moisture removal.

A further desirable feature of the present invention is the reversibility of the orthopaedic support such that the exterior fabric layer 26 may be brought into contact with the user's skin. In this case, increased heat retention is achieved as there are no channels provided on that side of the closed cell foam layer. Some breathing is still provided through the holes 28 but the orthopaedic support will tend to maintain more heat. This may be desirable for an initial warm up where the user desires the particular muscle or body part to be kept quite warm and once the user has effectively warmed up, the orthopaedic support can be reversed to reduce eat retention.

A modified orthopaedic support substrate is shown in FIG. 5 through FIG. 8. In this modified substrate 100, a 6 cm by 6 cm square grid, together with intersecting diagonals is used. The channels 102 are located on the grid and on the diagonals. Breathing ports 104 are at each intersection. The channels are preferably, approximately, 5 mm wide and the holes are of a similar diameter. The fabric material is displaced with the foam substrate and the rear surface of the channels 108 are displaced and protrude on the exterior surface 110 of the substrate (see FIG. 6). Triangular support islands 112 are formed and these islands preferably represent about 60 percent of the area of the support layer which engages the skin of the user. Some compression of the islands occurs but the channels generally remain open for venting to a hole and the outside air. As shown, even the centre of an island is not far from the cooling of a channel to provide dissipation about each island.

The substrate is preferably about 4 mm thick and the channels are displaced approximately this thickness. Some reduction of the thickness of the channels occurs as shown at 109. In this case, the substrate is reduced to about 3 mm thickness at the center of the channel.

The grid size is preferably increased or decreased to adjust the ratio of support area to cooling area. As the grid size is increased, the support area increases. Support area is preferably as large as possible while still providing effective cooling. The preferred range of support area is between 50 percent to 75 percent of the substrate area. The main design criteria is effective cooling which is achieved through the channels and holes. Holes alone reduce structural strength and render the support more prone to damage. Channels and holes provide an effective method for providing structural integrity and effective cooling. Other arrangements, other than grids, can also be used that allow effective venting and cooling beneath the orthopaedic support.

Figure 9:
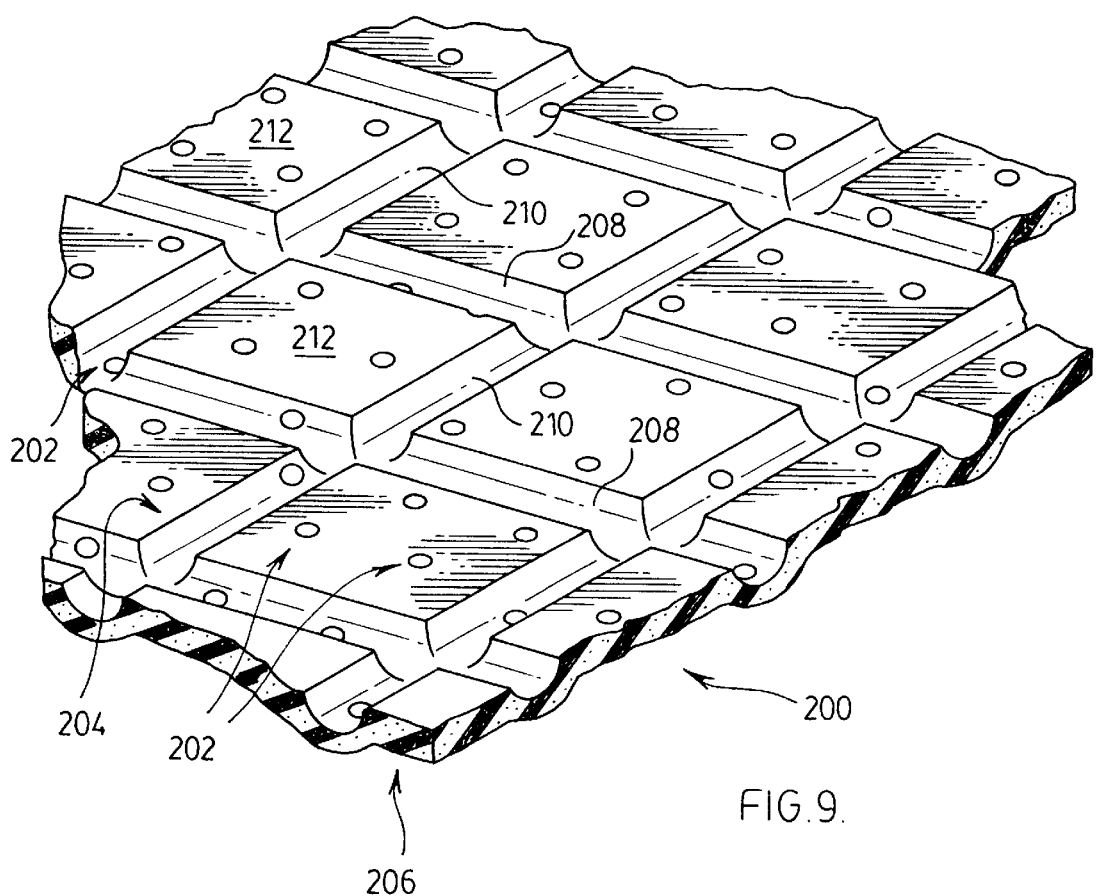
FIG. 9 is a partial perspective view of an alternate structure.

The cellular foam layer 200 shown in FIG. 9 is of a modified construction having a number of advantages with respect to breathability as well as accommodating various movements when worn by the user. A diamond type pattern extends longitudinally in the substrate with the diagonal channels 208, 210 defining the diamond shaped islands 212. A series of holes 202 perforate the substrate and these holes are located throughout the substrate with some of the holes occurring in the islands and some of the holes occurring within the channels. The substrate is preferably used by having the islands 212 face or come into contact with the skin of the user. In this regard it should be remembered that the interior surface 204 can include a breathable fabric layer thereon which thus contacts the user or the clothes of the user. The substrate has an exterior surface 206 which faces outwardly. This surface can also have a breathable fabric applied thereto.

The diagonal channels 208 and 210 extend outwardly of the substrate and the center of the channel is slightly compressed such that the thickness of the substrate is reduced.

The brace, when worn by the user, has improved breathability due to heat and moisture removal through the series of holes 202 and through the series of diagonal channels 208 and 210. The surface of the islands 210 provide substantial support or a load transfer surface with the body of the user. Heat is removed through the channels and there is an air pumping action due to movement of the user causing the channels 208 and 210 to expand and compress. Thus, movement of the user causes distortion of the brace and a pumping effect which improves the transfer of air through the substrate and the removal of heat and moisture through the substrate.

Preferably, the foam cellular substrate is approximately 4 mm thick and the series of holes are 1.5 to 2 mm in diameter. The holes are spaced one from the other, preferably about 8 mm. The sides of the diamonds are approximately 1.5 cm. Preferably the foam cellular layer 200 is a closed cell foam such as a neoprene. This type of substrate provides good strength and elasticity as well as good durability. Other foam cell layers can be used including open cell foam assuming the strength, elasticity and durability properties are sufficient for the particular application.

The series of holes 202 promote air transfer throughout the substrate and the small size and close spacing minimizes the possibility of hot spots due to poor venting.

The fabric layers shown in FIGS. 2 and 3 are also used with the substrate of FIG. 9 and preferably these fabric layers follow the contours of the layer 200. It is also preferable that the fabric layers be pierced by the holes, although this is not mandatory. With this system, the fabric layers can also provide a wicking type function where moisture associated with any of the islands is drawn towards the channels where more venting occurs.

During use, the substrate is wrapped about the body part of the user and some distortion of the channels 208 and 210 occurs. The channels are displaced outwardly from the interior surface of the substrate and remain out of contact with the user. In this way, the channels provide air gaps which during movement of the user distort due to contraction or expansion. This results in a pumping action which continuously occurs during movement by the user. Different user movements produce different deformation of the substrate and most movements result in an alternating distortion of the substrate.

The modified substrate of FIG. 9 provides a distributed support area namely the flat portions of the islands 212, which allow the channels 208 and 210 to remain essentially clear of the user. Venting of air into and out of the channel is freely accommodated by the series of holes and movement by the user encourages the exchange of air and the effect of moisture to the exterior of the substrate. The series of holes 202 also serve to allow transfer of moisture from the area beneath the support surfaces of the island 212 to the exterior of the substrate.

Although various preferred embodiments of the present invention have been described herein in detail, it will be appreciated by those skilled in the art, that variations may be made thereto without departing from the spirit of the invention or the scope of the appended claims.

The embodiment of the invention in which an exclusive property or privilege is claimed are defined as follows:

1. An orthopaedic support comprising a composite substrate for fastening about a body part and providing active support thereof, said composite substrate comprising an elastic foam substrate with a series of interconnecting channels in one side thereof and a series of holes through said foam substrate, at least some of said holes extending through said channels and providing heat dissipation by exchange of air moving through said channels and said holes; wherein said composite substrate includes a breathable fabric secured on art exterior surface of said foam substrate and a breathable layer secured on an interior surface.

2. An orthopaedic support as claimed in claim 1 wherein said series of holes are distributed throughout said composite substrate.

3. An orthopaedic support as claimed in claim 2 wherein each hole is of a diameter less than 2.0 mm.

4. An orthopaedic support as claimed in claim 2 wherein said orthopaedic support is reversible to alter heat retention characteristics of the orthopaedic support.

5. An orthopaedic support as claimed in claim 2 wherein said foam substrate is made of a neoprene.

6. An orthopaedic support as claimed in claim 2 wherein said channels are diagonal channels forming on one side of said substrate projecting support islands between said channels, and said channels project from an opposite side of said substrate.

7. An orthopaedic support as claimed in claim 6 wherein said channels are outwardly bowed and provide flex regions which expand or distort with body movement.

8. An orthopaedic support as claimed in claim 7 wherein said series of holes are less than approximately 2 mm in diameter.

9. An orthopaedic support as claimed in claim 8 wherein each support island has at least two holes of said series of holes passing through said island.

10. An orthopaedic support as claimed in claim 1 wherein said channels include longitudinal channels, lateral channels and diagonal channels.

11. An orthopaedic support as claimed in claim 1 wherein said series of holes are evenly distributed throughout said substrate.

12. An orthopaedic support as claimed in claim 1 wherein said channels occupy less than 40 percent of said foam layer.

* * * * *